United States Patent
Bortnick

(10) Patent No.: US 6,476,270 B2
(45) Date of Patent: Nov. 5, 2002

(54) WASTE-FREE PROCESS FOR MANUFACTURE OF AMIDES AND AMINES FROM CARBONIUM ION PRECURSORS AND NITRILES

(75) Inventor: Newman Mayer Bortnick, Oreland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 30 days.

(21) Appl. No.: 09/992,819

(22) Filed: Nov. 14, 2001

(65) Prior Publication Data

US 2002/0077505 A1 Jun. 20, 2002

Related U.S. Application Data

(60) Provisional application No. 60/254,862, filed on Dec. 12, 2000.

(51) Int. Cl.$^7$ .............................................. C07C 207/48
(52) U.S. Cl. ..................... 564/415; 564/490; 564/493
(58) Field of Search ................................ 564/415, 490, 564/493

(56) References Cited

U.S. PATENT DOCUMENTS 2,457,660 A * 12/1948 Gresham et al. ............ 564/125
2,601,387 A    6/1952 Gresham et al.

FOREIGN PATENT DOCUMENTS

| EP | 0099752 | 2/1984 | ......... C07C/102/08 |
| FR | 902342 | 8/1945 | |

OTHER PUBLICATIONS

Luzgin, Mikhail and Alexander G. Stepanov., "The Ritter reaction in zeolite H–ZSM–5. NMR observation if the intermediate N–alkylnitrilium cation formed on interaction between Bu$^r$OH and MeCN", Medeleev Commun., pp. 238–239 (1996).

Firouzabadi et al., "Highly Selective Admiration of Benzylic Alcohols With Nitriles. A Modified Ritter Reaction.", Synthetic Communications, 24(5) pp. 601–607 (1994).

Olah et al., "Nafion–H$^R$ Catalized Baeyer–Villiger Oxidation and Ritter Reaction (1)", Materials Chemistry and Physics, 17, pp. 21–30 (1987).

* cited by examiner

*Primary Examiner*—Brian J. Davis
(74) *Attorney, Agent, or Firm*—Kenneth Crimaldi

(57) ABSTRACT

A method for preparation of an amine from a carbonium ion precursor and a nitrile. The method comprises the steps of: (a) contacting the carbonium ion precursor and the nitrile with aqueous ammonium hydrogen sulfate to produce an amide; and (b) hydrolyzing the amide to the amine. Optionally, the ammonium hydrogen sulfate, nitrile and ammonia are recovered and recycled.

7 Claims, No Drawings

WASTE-FREE PROCESS FOR MANUFACTURE OF AMIDES AND AMINES FROM CARBONIUM ION PRECURSORS AND NITRILES

CROSS REFERENCE TO RELATED PATENT APPLICATIONS

This is a non-provisional application of prior pending U.S. provisional application Ser. No. 60/254,862 filed Dec. 12, 2000.

BACKGROUND

This invention relates generally to a process for conversion of carbonium ion precursors and nitrites to amines.

U.S. Pat. No. 2,457,660 discloses a process for preparation of N-tertiary alkyl amides from carbonium ion precursors and nitrites in the presence of an acidic catalyst. The list of suitable acidic catalysts includes ammonium bisulfate. This reference does not disclose a process for conversion of the amides to the corresponding amines.

The problem addressed by this invention is to reduce the need for a strong acid catalyst in a process for conversion of carbonium ion precursors and nitriles to amines.

STATEMENT OF INVENTION

In one embodiment, the present invention is a method for preparation of an amine from a carbonium ion precursor and a nitrile. The method comprises the steps of: (a) contacting the carbonium ion precursor and the nitrile with aqueous ammonium hydrogen sulfate to produce an amide; and (b) hydrolyzing the amide to the amine.

In another embodiment, the present invention is directed to a substantially waste-free method for preparation of an amide from a carbonium ion precursor and a nitrile. The method comprises the steps of (a) contacting the carbonium ion precursor and the nitrile with aqueous ammonium hydrogen sulfate to produce an amide; (b) recovering diammonium sulfate from an aqueous phase; and (c) decomposing diammonium sulfate by heating to produce ammonia and ammonium hydrogen sulfate.

DETAILED DESCRIPTION

An "alkyl" group is a saturated hydrocarbyl group having from one to twenty carbon atoms in a linear, branched or cyclic arrangement. Substitution on alkyl groups of one or more halo or alkoxy groups is permitted; alkoxy groups may in turn be substituted by one or more halo substituents. Preferably, alkyl groups contain from one to twelve carbon atoms. Preferably, alkyl groups have no halo or alkoxy substituents. An "alkenyl" group is an "alkyl" group in which at least one carbon-carbon single bond has been replaced with a double bond. An "aryl" group is a substituent derived from an aromatic hydrocarbon compound. An aryl group has a total of from six to twenty ring atoms, and has one or more rings which are separate or fused. Substitution on aryl groups of one or more halo, alkyl, alkenyl or alkoxy groups is permitted, with substitution by one or more halo groups being possible on alkyl, alkenyl or alkoxy groups. An "aralkyl" group is an "alkyl" group substituted by an "aryl" group.

A "carbonium ion precursor" is a species capable of generating a carbonium ion in the presence of an acid. Preferred carbonium ion precursors include alkenes capable of forming carbonium ions upon protonation, as well as the alcohols, ethers and esters, which, upon protonation and elimination, form the same carbonium ion as the alkene, especially the alkyl ethers and esters of alkyl carboxylic acids. For example, isobutylene, tert-butanol, tert-butyl methyl ether and tert-butyl acetate all are capable of forming tert-butyl cation. Benzyl alcohols, benzyl methyl ethers, benzyl halides and benzyl acetates are capable of forming benzyl cations.

Preferred alkenes are those having the formula $R_1R_2C=CR_3R_4$, wherein $R_1$ is alkyl, aryl or aralkyl; $R_2$ is hydrogen, alkyl or aralkyl, or $R_1$ and $R_2$ form a ring having five or six ring atoms with the alkene carbon to which they are attached; $R_3$ and $R_4$ are independently hydrogen or alkyl, or $R_1$ and $R_3$ form a ring having five or six ring atoms with the two alkene carbons. Alcohols, ethers and esters corresponding to these alkenes also are preferred, as described above; for example, compounds of the formulas $R_1R_2C(OX)-CHR_3R_4$ and $R_1R_2HC-C(OX)R_3R_4$, where X is hydrogen, alkyl or alkylcarbonyl. Specific examples of preferred alkenes are propylene, 1- and 2-butenes, isobutylene, trimethylethylene, tetramethylethylene, propylene dimers, 3,5,5-trimethyl-1-pentene, 3,5,5-trimethyl-2-pentene, propylene trimers, propylene tetramers, isobutylene trimer, propylene pentamers and hexamers, 1-octene, cyclohexene, 1-methylcyclohexene, styrene, α-methylstyrene, dicyclopentadiene, α-pinene, β-pinene, camphene, norbornene, norbornadiene and menthadienes.

A "nitrile" is a compound containing a nitrile group, said compound being either an organic nitrile compound or hydrogen cyanide. Preferred nitrites, RCN, are those in which R is hydrogen, methyl, phenyl, benzyl, other alkyl, alkaryl, other aryl, vinyl, α-methylvinyl, and cyclohexyl. The most preferred nitrile is hydrogen cyanide.

The molar ratio of the nitrile to the carbonium ion precursor preferably is at least 1, and more preferably is in the range from 2 to 20, still more preferably from 3 to 10, and most preferably from 5 to 10. The molar ratio of the carbonium ion precursor to ammonium hydrogen sulfate is preferably from 1 to 100, more preferably from 4 to 20. The preferred ratio of carbonium ion precursor to water is from 1 to 10, more preferably from 2 to 5.

The reaction of the carbonium ion precursor with the nitrile preferably is carried out at a temperature from 60° C. to 225° C., more preferably from 80° C. to 225° C., and still more preferably from 80° C. to 200° C. The reaction is allowed to progress for a period of time sufficient to ensure substantial conversion of the carbonium ion precursor to the amide. Preferably, the reaction time is in the range from about 0.1 hour to 12 hours, more preferably from 1 hour to 8 hours. At temperatures above 100° C., hydrolysis of the amide to the amine proceeds quickly, so that temperatures in the range from 100° C. to 225° C. are preferred for direct conversion from the initial starting materials to the amine, and temperatures in the range from 130° C. to 225° C. are further preferred. Preferably, the carbonium ion precursor and the nitrile are contacted at a pressure greater than atmospheric pressure to keep the reactants substantially in the liquid phase, for example, by heating the reactants under autogenous pressure. When the conditions allow rapid hydrolysis of the amide to the amine, and ammonium hydrogen sulfate is the hydrolysis catalyst, the process may be run continuously to produce an amine product, for example, in a plug-flow tubular reactor.

In one embodiment of the invention, the reaction is stopped when the product is largely in the form of the amide, before substantial hydrolysis to the amine has occurred. In this embodiment, ammonia preferably is added to neutralize any amine salts that have formed. The aqueous phase is distilled to strip any excess ammonia, and ammonium carboxylate, if present. The ammonium carboxylate can be dehydrated to recover the starting nitrile, as described below. Continued distillation of the aqueous phase leads to decomposition of diammonium sulfate to ammonium hydrogen sulfate and ammonia. The recovered ammonium hydrogen sulfate and ammonia, along with any recovered nitrile, can be recycled, thereby creating a substantially waste-free process for production of an amide.

In another embodiment of the invention, the amide is hydrolyzed to amine salts in the presence of a hydrolysis catalyst, preferably an acidic catalyst. The preferred molar ratio of water to amide is from 5 to 50, most preferably from 5 to 20. The preferred reaction temperature for hydrolysis is from 100° C. to 250° C., more preferably from 130° C. to 250° C., still more preferably from 130° C. to 225° C., and most preferably from 150° C. to 225° C. The reaction is allowed to progress for a period of time sufficient to ensure substantial conversion of the amide to amine salts. Preferably, the reaction time is in the range from about 0.5 hour to 12 hours, more preferably from 1 hour to 10 hours. Optionally, additional ammonium hydrogen sulfate or another hydrolysis catalyst is added. Preferably, if another hydrolysis catalyst is added, the amide is first separated from the ammonium hydrogen sulfate present from the amide formation. Preferably, the hydrolysis is performed without addition of a hydrolysis catalyst other than ammonium hydrogen sulfate.

Following the hydrolysis, the amine is present largely as an aminium carboxylate salt in an aqueous phase. In one embodiment of the invention, excess ammonia is added to release the free amine to an organic phase. Optionally, an organic water-immiscible solvent is added to extract the amine. Preferably, the organic phase is fractionally distilled to recover the ammonia and the amine. Preferably, the molar ratio of ammonia to the carbonium ion precursor is in the range from about 1 to 10, more preferably from 2 to 6, and most preferably from 3 to 5. This also produces a mixture of ammonium carboxylate and diammonium sulfate in the aqueous phase. In one embodiment of the invention, the aqueous phase is distilled to recover first excess ammonia, and then ammonium carboxylate. Thereafter, decomposition of diammonium sulfate to ammonium hydrogen sulfate and ammonia occurs. The recovered ammonium hydrogen sulfate and ammonia can be recycled.

In one embodiment of the invention, the ammonium carboxylate is dehydrated to the starting nitrile, which can be recovered by distillation. Optionally, the recovered nitrile is recycled. Preferably, the dehydration is performed by contactin ammonium carboxylate with activated alumina at a temperature from 300° C. to 450° C. Preferably, the dehydration is performed in the presence of ammonia gas.

Practicing the method for production of an amine with all of its various embodiments, and without addition of a hydrolysis catalyst other than ammonium hydrogen sulfate leads to a substantially waste-free process. The net result of this process is that an amine is produced from a carbonium ion precursor and a nitrile, while the ammonium hydrogen sulfate, ammonia and nitrile all are recovered and recycled. This five-step process is illustrated for a carbonium ion precursor, $R_1R_2C=CH_2$, in the scheme shown below:

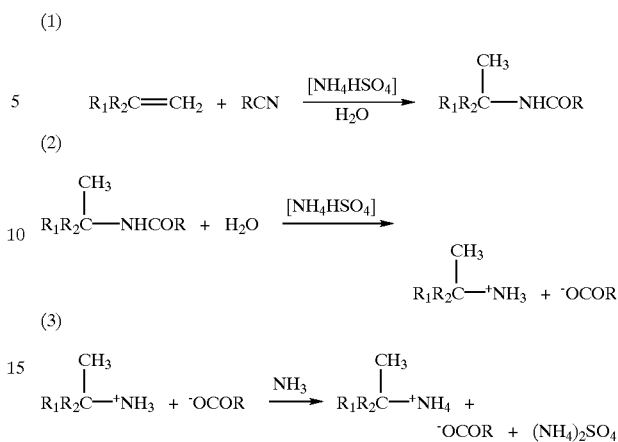

What is claimed is:

1. A method for preparation of an amine from a carbonium ion precursor and hydrogen cyanide; said method comprising steps of:
   (a) contacting the carbonium ion precursor and hydrogen cyanide with aqueous ammonium hydrogen sulfate at a pressure greater than atmospheric pressure to produce an amide;
   (b) hydrolyzing said amide to the amine to the amine without addition of a hydrolysis catalyst other than ammonium hydrogen sulfate; and
   (c) recovering diammonium sulfate and decomposing it by heating to produce ammonia and ammonium hydrogen sulfate.

2. The method of claim 1 in which ammonium formate is recovered and dehydrated to produce hydrogen cyanide.

3. The method of claim 2 in which the carbonium ion precursor is an alkene of formula $R_1R_2C=CR_3R_4$, wherein $R_1$ is alkyl, aryl or aralkyl; $R_2$ is hydrogen, alkyl or aralkyl, or $R_1$ and $R_2$ form a ring having five or six ring atoms with the alkene carbon to which they are attached; $R_3$ and $R_4$ are independently hydrogen or alkyl, or $R_1$ and $R_3$ form a ring having five or six ring atoms with the two alkene carbons.

4. A method for preparation of an amide from a carbonium ion precursor and a nitrile; said method comprising steps of:
   (a) contacting the carbonium ion precursor and the nitrile with aqueous ammonium hydrogen sulfate to produce an amide;
   (b) recovering diammonium sulfate from an aqueous phase; and
   (c) decomposing diammonium sulfate by heating to recover ammonia and ammonium hydrogen sulfate.

5. The method of claim 4 which the carbonium ion precursor, the nitrile and the ammonium hydrogen sulfate are contacted at a pressure greater than atmospheric pressure.

6. The method of claim 5 in which the nitrile is hydrogen cyanide.

7. The method of claim 6 in which the carbonium ion precursor is an alkene of formula $R_1R_2C=CR_3R_4$, wherein $R_1$ is alkyl, aryl or aralkyl; $R_2$ is hydrogen, alkyl or aralkyl, or $R_1$ and $R_2$ form a ring having five or six ring atoms with the alkene carbon to which they are attached; $R_3$ and $R_4$ are independently hydrogen or alkyl, or $R_1$ and $R_3$ form a ring having five or six ring atoms with the two alkene carbons.

* * * * *

UNITED STATES PATENT AND TRADEMARK OFFICE
CERTIFICATE OF CORRECTION

PATENT NO. : 6,476,270 B2  Page 1 of 1
DATED : November 5, 2002
INVENTOR(S) : Newman Mayer Bortnick It is certified that error appears in the above-identified patent and that said Letters Patent is hereby corrected as shown below:

Column 1,
Line 15, delete "nitrites" and insert -- nitriles --;
Line 18, delete "nitrites" and insert -- nitriles --;

Column 2,
Line 29, delete "nitrites" and insert -- nitriles --;

Column 3,
Line 55, "contactin" should read -- contacting --;

Column 4,
equation (3) should read as follows:
--

--

Line 29, delete "to the amine" (second occurrence);

Signed and Sealed this

Eighteenth Day of February, 2003

JAMES E. ROGAN
*Director of the United States Patent and Trademark Office*